United States Patent [19]

Burke et al.

[11] Patent Number: 5,517,994
[45] Date of Patent: May 21, 1996

[54] SELF DIAGNOSTIC ULTRASONIC IMAGING SYSTEMS

[75] Inventors: Thomas M. Burke, Bothell; James Mehi, Kirkland, both of Wash.

[73] Assignee: Advanced Technology Laboratories, Inc., Bothell, Wash.

[21] Appl. No.: 340,562

[22] Filed: Nov. 16, 1994

[51] Int. Cl.⁶ .......................................... A61B 8/00
[52] U.S. Cl. ........................ 128/660.01; 128/660.07
[58] Field of Search .................. 128/660.01, 660.07; 73/1 DV

[56] References Cited

U.S. PATENT DOCUMENTS

| | | | |
|---|---|---|---|
| 4,233,677 | 11/1980 | Brown et al. | 367/13 |
| 4,366,561 | 12/1982 | Klein | 367/77 |
| 4,475,376 | 10/1984 | Keilman | 73/1 DV |
| 4,545,251 | 10/1985 | Uchida et al. | 73/631 |
| 4,603,702 | 8/1986 | Hwang et al. | 128/660.01 |
| 4,694,680 | 9/1987 | Takeuchi et al. | 128/660.01 |
| 4,708,127 | 11/1987 | Abdelghani | 601/2 |
| 4,791,915 | 12/1988 | Barsotti et al. | 601/2 |
| 4,867,168 | 9/1989 | Stoor et al. | 128/660.01 |
| 4,945,767 | 8/1990 | Shirasaka | 73/610 |
| 5,230,339 | 7/1993 | Charlebois | 128/660.01 |

Primary Examiner—Francis Jaworski
Attorney, Agent, or Firm—W. Brinton Yorks, Jr.

[57] ABSTRACT

A method and apparatus are described for testing the integrity of an ultrasonic transducer probe or the ultrasound system connected to the probe. The elements of the transducer are pulsed at a time when the probe is not in contact with a patient and the surface of the probe lens is exposed to the open air. The channel electronics receives the echo signal returned from the lens-air interface and reverberations between this interface and the transducer. These signals are analyzed by a diagnostic processor coupled to the channel electronics for characteristics such as amplitude, time of echo reception, group delay, and other characteristics to determine the possible existence of problems such as faulty transducer elements or connections and problems in the system receive electronics. The diagnostic processor can adaptively adjust an operating characteristic of the system electronics such as gain or time delay to compensate for a detected out of tolerance condition.

17 Claims, 5 Drawing Sheets

SELF DIAGNOSTIC ULTRASONIC IMAGING SYSTEMS

This invention relates to improvements in ultrasonic diagnostic imaging systems, and in particular to ultrasonic imaging systems capable of performing self diagnosis of an ultrasonic transducer probe and the channel electronics connected to elements of the transducer.

Ultrasonic diagnostic systems are operable with a variety of ultrasonic transducer probes which are specially adapted to perform specific diagnostic procedures. Many probes utilize multielement transducers to shape and steer the transmitted ultrasonic waves, and to receive echo signals across an aperture formed by a plurality of the transducer elements. The received echo signals are processed by the ultrasound system which controls the activation of the transducer and processes the received echo information to form an image or measure a physiological condition of the body such as the state of flow in vessels of the body. The individual elements are electrically connected to individual channels of a processor known as a beamformer. Each channel of the beamformer controls the time of activation of its respective transducer element and appropriately delays the echo signals received by a transducer element to bring the echo signal components received by the transducers into time coincidence. The time aligned echo signal components can then be combined to form a coherently focused echo signal. The coherent echo signal can then be detected and further processed as a contributor to a spatial image of the interior of the body or to measure flow and other functions of the body.

Ultrasonic probes and systems, like other complex electronic medical devices, can develop fault with extended use and wear. The channels of the ultrasound system which control the transducer and process the echo signals can malfunction due to power fluctuations, component aging, or other electrical hazards. The probes themselves will age and wear with continual use and can fail or break if dropped severely. Often these faults and failures are manifestly apparent. The probe or system will simply fail completely. But some problems, such as the failure of a single element of a multielement probe or a single channel of a multichannel system, are more subtle and not immediately observable by a user. Such undetected failures can lead to a degradation in diagnostic performance which is difficult to detect or remedy. It would be desirable for an ultrasound system to be capable of self diagnosing such subtle problems in both the system and the probes connected to the system.

In accordance with the principles of the present invention an ultrasonic diagnostic system is provided which is capable of performing self diagnostic tests on the system processing and control channels coupled to the transducer elements of an ultrasonic probe, and on the ultrasonic probes connected to the system. These self diagnostic tests are performed by a diagnostic processor which activates the transducer elements of an idle ultrasonic probe transmitting into the open air. When activated in this manner a surface reflection is returned from the probe-air interface and is received and processed, and the resultant signals are analyzed by the diagnostic processor on a channel by channel basis. The characteristics of the received signals reveal certain operational conditions of the probe and the channels connected to the probe, and these conditions can be reported to the user or to service personnel.

Figure 1:
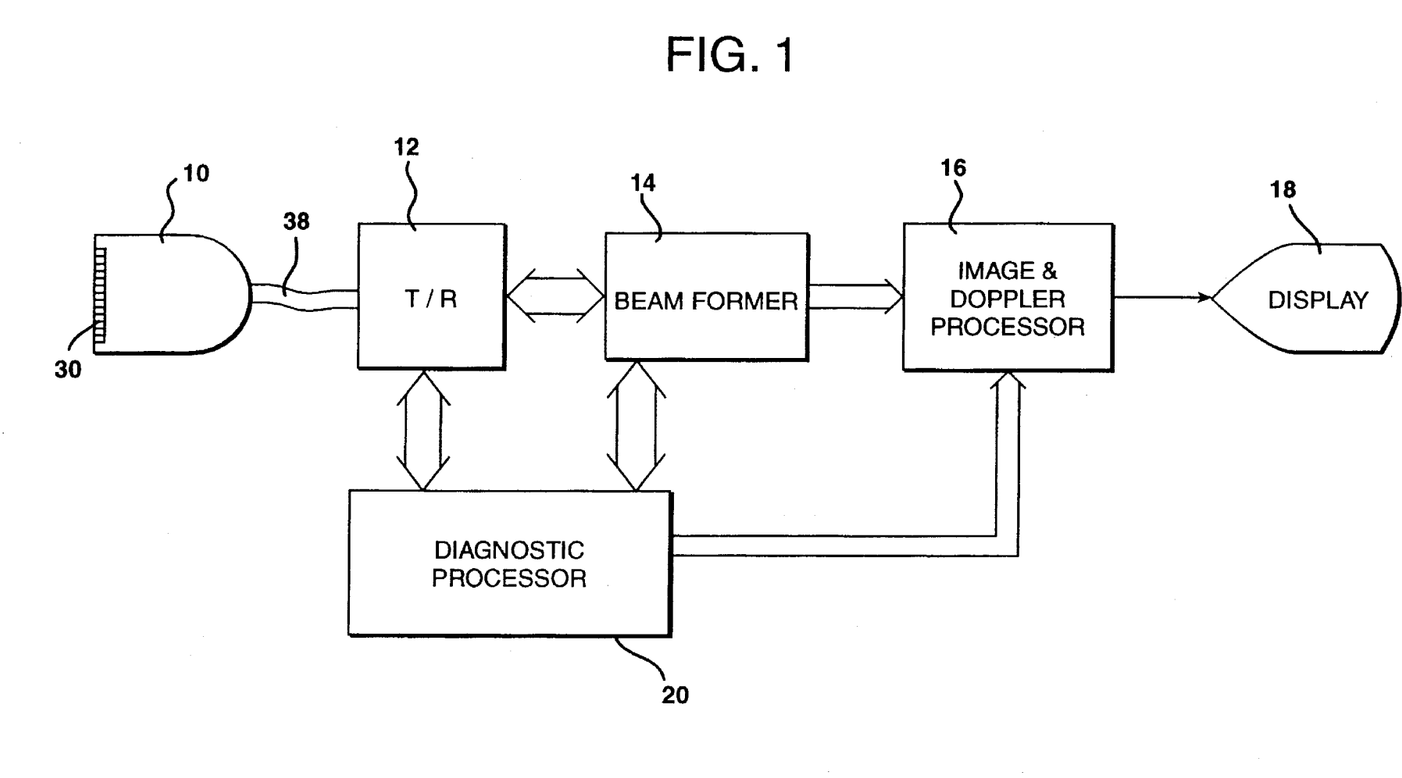
FIG. 1 is a block diagram of an ultrasonic probe and ultrasound system constructed in accordance with the principles of the present invention.

Referring first to FIG. 1, the block diagram of an ultrasonic diagnostic system constructed in accordance with the principles of the present invention is shown. An ultrasonic probe 10 includes a multielement transducer 30. Each element of the transducer 30 is connected by a conductor of a multiconductor cable 38 to a probe transmitter and receiver 12. The transmitter and receiver 12 includes a number of piezoelectric drivers which are controlled by a beamformer 14 to pulse individual elements of the transducer 30 at the appropriate times and with the appropriate waveforms to form and steer a transmitted ultrasonic wave into the body of a subject. In the receive mode the transmitter and receiver 12 receives the echo signals produced by each transducer element, converts the received signals to streams of digital signal samples, and couples to digital signal samples to a digital beamformer 14. The digital beamformer includes a number of separate, parallel channel, each of which is connected to receive the digital signal samples produced by an element of the transducer. The digital beamformer 14 applies an appropriate delay to the signals of each transducer element which brings the echo components received by the transducer elements from a given reflector into time coincidence. The delayed digital signal samples of the respective channels are summed to form a coherent digital echo signal. The coherent digital echo signals are processed by an image & Doppler processor 16 to form a diagnostic image or to make a diagnostic measurement such as the velocity of blood flow in the subject's body, as desired by the user. The resultant image or measurement is then displayed on a display 18.

In accordance with the principles of the present invention a diagnostic processor 20 is coupled to a number of the aforementioned subsystems, including the transmitter and receiver 12, the beamformer 14, and the image & Doppler processor 16. The diagnostic processor 20 operates under the control of or in conjunction with a central system controller (not shown) which controls the previously described subsystems in the performance of their active diagnostic functions. During times when the ultrasound system is not in diagnostic service, or when commanded by the user or service personnel, the diagnostic processor performs self diagnostic tests on the ultrasonic probe 10, the transmitter and receiver 12, and the beamformer 14. When activated the diagnostic processor causes the beamformer to sequentially pulse each individual element of the transducer. The diagnostic processor then commands the transmitter and receiver and the beamformer to receive and process the echoes returned from the probe-air interface and reverberations thereof. This echo information is analyzed by the diagnostic processor on an individual channel basis and comparatively between channels to determine whether the probe or the subsystems of the ultrasound system are experiencing any faults or malfunctions.

A principle of the present invention is the activation of the ultrasonic probe when the acoustic aperture of the probe is exposed to the open air, for it is reflections from the probe-air interface which are analyzed by the diagnostic processor. This self testing can be performed automatically when the ultrasound system is not in diagnostic use and a probe is connected to the system and passively hanging in the system's probe holder. For greatest test accuracy it is necessary that the surface of the acoustic window be clean. As ultrasonic diagnosis usually involves the use of ultrasonic couplant gel between the acoustic window and the patient, this means that the test will be most accurate when residual gel has been cleaned from the probe. This ensures that the probe-air interface is the surface of the lens covering the transducer and not the irregular surface of gel coating the lens.

Figure 5:
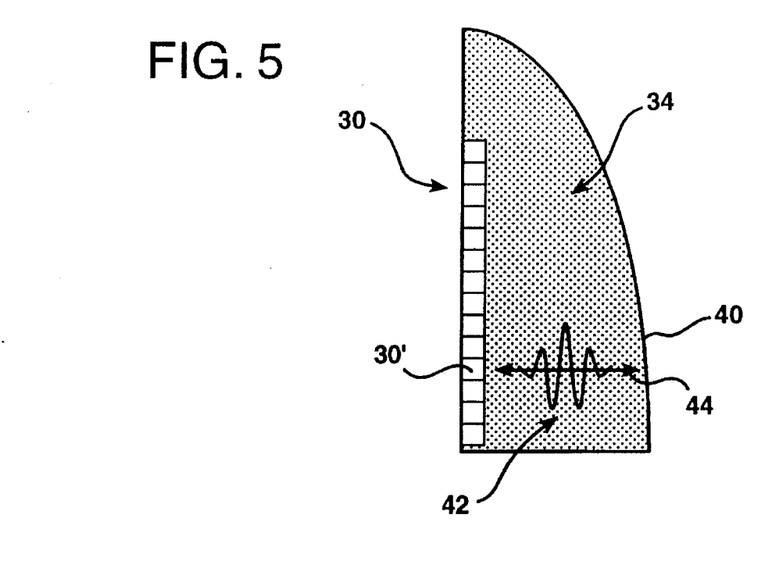
FIG. 5 is a diagram of a multielement transducer and lens which illustrates the principle of the self diagnostic testing of the present invention.

The principle of the present invention is illustrated by reference to FIG. 5. This drawing shows a row of elements 30 of a multielement transducer, one of which is designated as 30'. Overlaying the transducer elements is an acoustic lens 34. The lens 34 can be (as will be described below) comprised of different layers of different materials, and can serve a number of purposes. It can serve to electrically insulate the medical patient from the electrodes of the transducer. It can acoustically shape the transmitted and received ultrasonic waves. It can match the acoustic impedance of the transducer to the acoustic impedance of the body. In FIG. 5 the surface of the lens 34, the probe-air interface, is designated by reference numeral 40.

To perform a diagnostic test one element of the transducer such as element 30' is pulsed by the ultrasound system. The element 30' emits an ultrasonic pulse 42 in the direction of arrow 44. Some of the energy of the ultrasonic pulse passes into the air at the probe-air interface 40, but most of the energy is reflected by the interface 40 back to the transducer element 30'. When the reflected pulse reaches the element 30' it will generate a piezoelectric response in the element, and this response is coupled to the ultrasound system and processed as described below. A portion of the energy of the pulse is reflected from the surface of the transducer and travels outward again, repeating the reflection cycle. These reverberations between the transducer and the probe-air interface can also be received and processed by the diagnostic processor.

Figure 2:
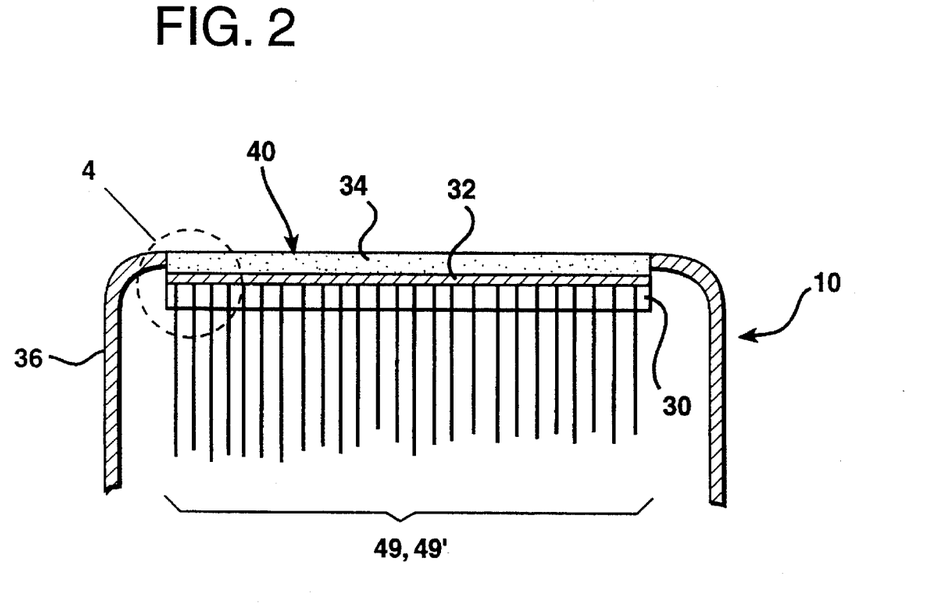
FIG. 2 is a cross-sectional view of the acoustic window of a multielement ultrasonic transducer probe.

FIG. 2 is a cross-sectional view of the acoustic window of a multielement ultrasonic transducer probe 10. The outer surface of the probe 10 is defined by the probe case 36 and the outer surface of an RTV rubber acoustic lens 34. The acoustic lens 34 covers an acoustic matching layer 32 which matches the acoustic impedance of the transducer to that of the acoustic lens and tissue. The matching layer 32 overlays the transducer elements 30 which have electrodes plated on their outer and inner surfaces. A number of conductors 49, 49' extend from the transducer electrodes and are joined to individual conductors of the cable 38. The volume behind the transducer 30 and shown occupied by the conductors 49, 49' is filled with acoustic damping material which damps acoustic energy emanating from the back of the transducer.

Figure 3A:
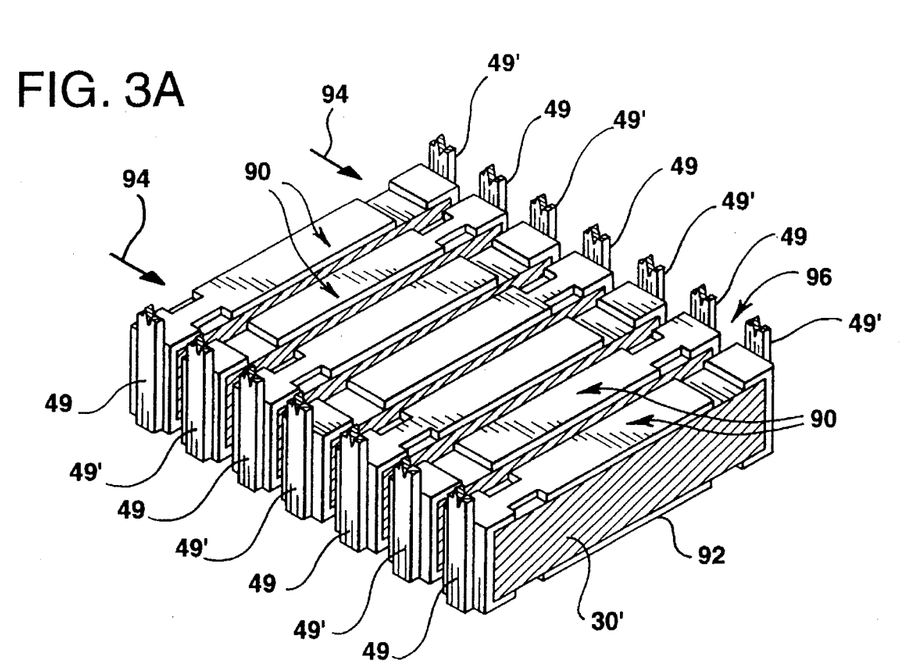
FIGS. 3a and 3b illustrate the construction of the transducer elements and transducer electrodes of the ultrasonic probe of FIG. 2.
Figure 3B:
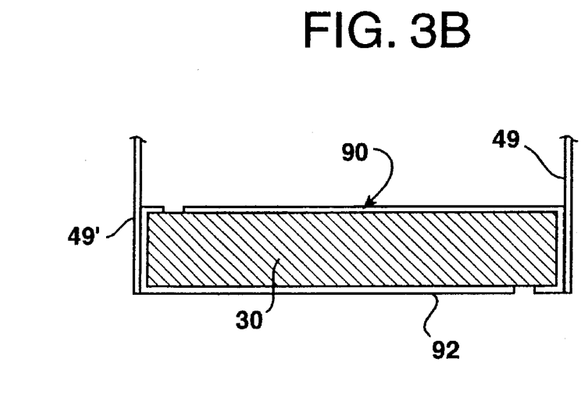

A preferred construction of the transducer 30 and its electrodes is shown in FIGS. 3a and 3b. A plate of piezoelectric ceramic is initially covered on its two planar surfaces and edges with a metallized electrode coating. Laser cutting or photolithography is then used to form holes in the electrode coating in the longitudinal directions indicated by arrows 94. The ceramic plate and its metallized coating are then diced into individual transducer elements 30' and electrodes 90, 92 by transverse dicing as indicated by arrow 96. The result is a series of transducer elements and electrodes as shown in FIGS. 3a and 3b. Signal electrodes 90 are located on the back surface of the transducer 30 and wrap around one end of the transducer elements. Return electrodes 92 are located on the outer planar surface of the transducer and wrap around the other end of the transducer elements as shown in FIG. 3a. Metallic fingers 49, 49' are attached to the electrodes at the ends of each element, and extend to their points of connection with conductors of the cable 38.

The laser formed cuts and notches result in an alteration of the signal and return ends of the transducer elements from one element to another. That is, metallic fingers 49 are connected to signal electrodes 90, and interspersed metallic fingers 49' are connected to return electrodes 92. The alternating patterns are offset from one end of the transducer to the other, since each signal finger must oppose a return finger on the other end of each element. The alternation of signal and return connections helps to reduce crosstalk between electrodes and connections.

Figure 4:
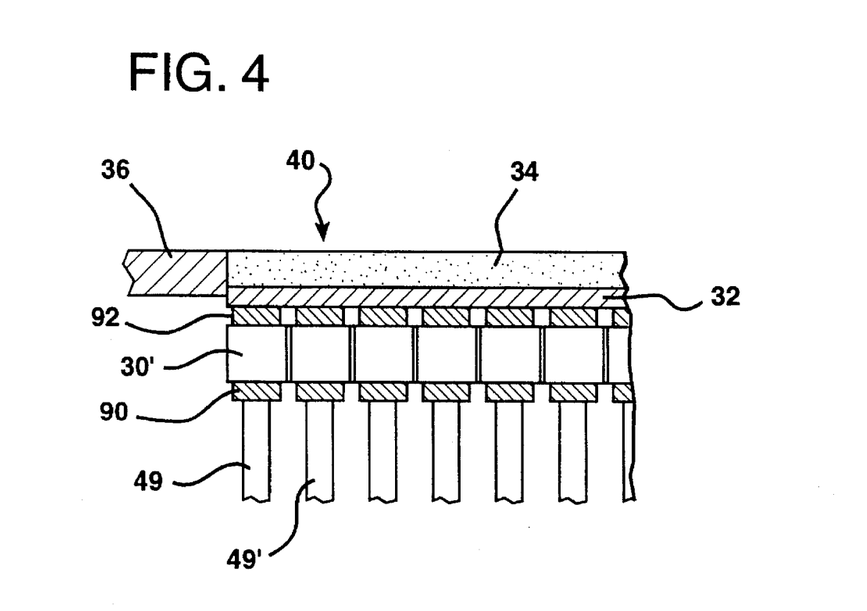
FIG. 4 is an enlarged cross-sectional view the transducer elements and lens of the ultrasonic probe of FIG. 2.

This transducer and electrode assembly is overlaid with the matching layer 32 and the acoustic lens 40 as shown in the enlarged cross-sectional view of FIG. 4.

In performing the self diagnostic test of the present invention one element 30' of the probe is actuated by a transducer driver of the transmitter and receiver 12 under control of the diagnostic processor 20. A pulse is thereby transmitted to the probe-air interface 40 of the probe. In the case of a probe constructed as shown in FIGS. 2–4, the pulse will travel through the matching layer and acoustic lens 34 to reach the probe-air interface, a distance of approximately 0.5–1.0 mm in the typical ultrasonic probe. At the speed of sound typical for the matching layer and lens materials it will take about 500–1000 nsec. for the pulse to reach the probe-air interface 40, and another 500–1000 nsec for the reflection to return to the transducer element 30'. Thus, a properly operating probe and receiver is expected to produce a first echo return after 1–2 μsec., and subsequent attenuated reflections at 1–2 μsec. intervals thereafter.

Figure 6:
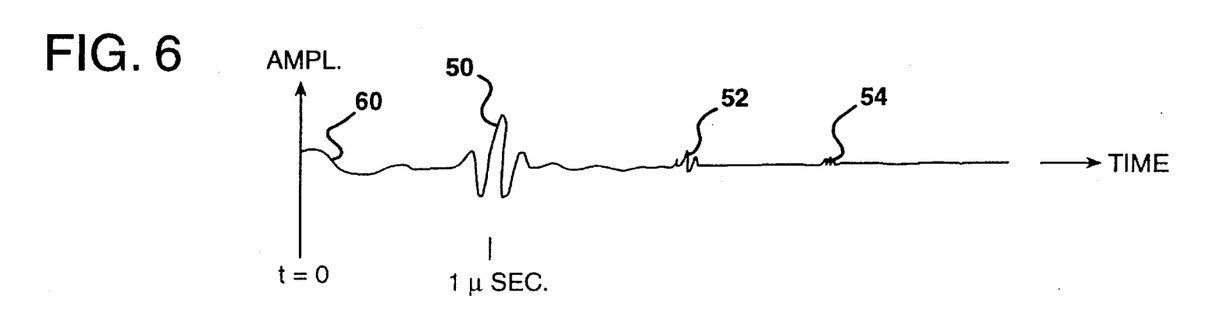
FIG. 6 shows a representative waveform which is analyzed by a diagnostic processor of the present invention.

FIG. 6 illustrates a typical waveform that would be expected from these reflections from the probe-air interface of the probe. At time t=0 the transducer element 30' transmits a pulse and 1 μsec. later an echo 50 is received by the transducer element from the probe-air interface and processed by the channel of the ultrasound system that is connected to that element. After passage of another microsecond another reflection 52 of the pulse is received, and after passage of a further interval of 1 μsec. another echo 54 is received, each attenuated more greatly than the previous pulse.

In practice however the receiver of the transmitter and receiver 12 may be saturated by transmit pulse energy when activated immediately after application of a drive pulse to the transducer element. As a consequence the received signal waveform can exhibit some ringing as shown at 60 in FIG. 6 which will quickly damp and dissipate as the receiver returns to linear operation. When the actuated transducer element 30' and associated channel of the beamformer are operating properly, the diagnostic processor 20 can expect to receive a waveform (either in analog or digital form) similar to that of FIG. 6. The waveform will appear as shown in the drawing at the output of the transmitter and receiver 12 prior to incurring any beamformer delay. A time delayed version of the received waveform will appear at the output of the beamformer 14, with the delay being that imparted by the associated beamformer channel. The diagnostic processor can be programmed to run the test several times under different beamformer delay conditions. A first test can be run with the beamformer channel programmed for its minimum delay and a second test can be run with the beamformer channel programmed for its maximum delay. During each test the other channels of the beamformer are inhibited so that the output of the beamformer will be the delayed signal produced by only the particular transducer element and channel then being tested.

The test results of a particular transducer element and channel are stored and compared with the test results of other channels and elements. The amplitudes of the waveforms from channel to channel should be within a given range of tolerance, for instance. The variation of the amplitude of the signal of one channel would indicate that the gain of the receiver or beamformer of that channel is out of tolerance, for example. The diagnostic processor 20 can be controlled if desired in such a situation to compensate for such variation. The test of a given transducer element can be re-run with another receiver and beamformer channel switched to connect to the transducer element to see if the waveform amplitude variance is present with a different receiver and beamformer channel. A comparison of the initial and second test of the element will isolate the condition to the transducer probe or the electronics of the receiver. In either case the gain of an amplifier in the receiver or beamformer for the channel connected to the element can be adjusted under control of the diagnostic processor to compensate for the amplitude variation.

If there is a problem with the transducer element or beamformer channel being tested, a waveform different from that shown in FIG. 6 will be received. For instance, if the beamformer channel has failed, the waveform at the output of the beamformer will not simply be a delayed replica of the received waveform produced at the output of the transmitter and receiver 12. It may be that there is no signal at the output of the beamformer, or that the beamformer output waveform is badly distorted as compared with the input waveform. A comparison of the beamformer input and output waveforms is made by the diagnostic processor 20 to determine whether the beamformer channel for the particular transducer element is operating within its specifications.

Another possibility is a malfunction within the probe. For instance, the conductors between the transducer element and the ultrasound system could have come loose or opened. This will mean that the transmitter and receiver 12 is driving an open circuit which is no longer terminated by the transducer element. In this case the receiver will only see the effect of saturation of the driver; it will not see the ringing effect of the transducer element or any received echo signals. The received waveform will appear similar to that in FIG. 7a, a smoothly decaying waveform with no r.f. content. When this signal is analyzed by the diagnostic processor the processor will report an open circuit to the transducer element being tested.

Another possibility is that the receiver in the transmitter and receiver 12 has malfunctioned due to a short circuit. If the receiver channel for the particular transducer element has short circuited, the analog to digital converter at the output of the transmitter and receiver 12 in a digital system will exhibit the step response shown in FIG. 7b. Upon receipt of such a waveform the diagnostic processor 20 will conclude that there is a problem with the receiver in the particular channel being tested.

Figure 7A:
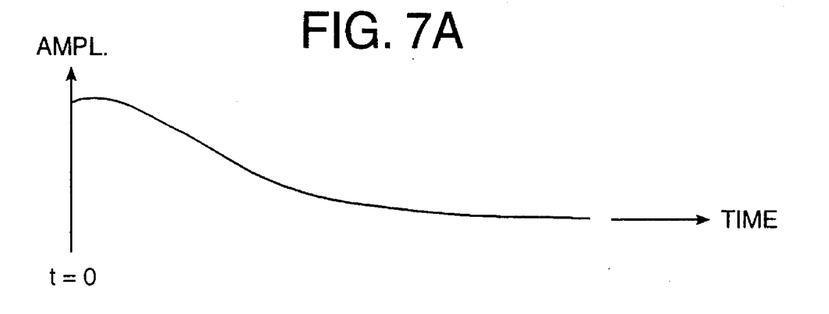
FIGS. 7a–7c show representative waveforms of certain fault conditions which are analyzed by a diagnostic processor of the present invention.
Figure 7B:
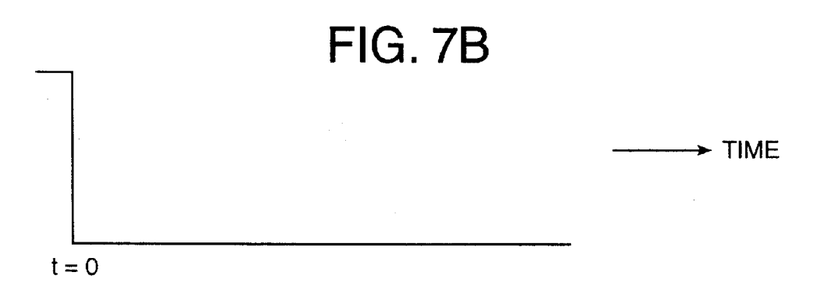
Figure 7C:
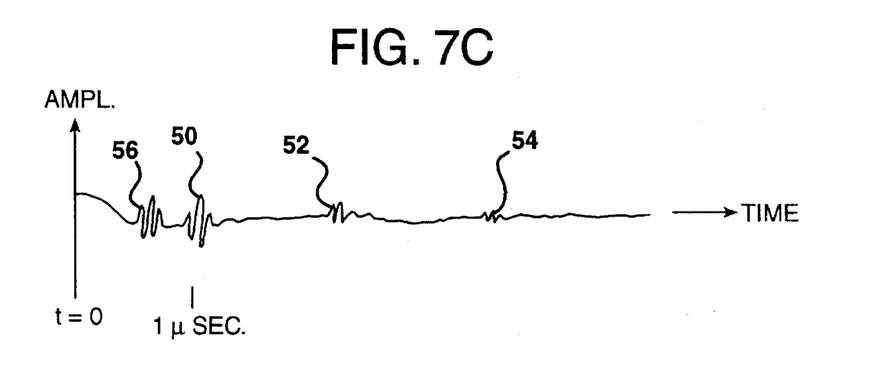

A further possibility is that a delamination has occurred between the layers of materials between the transducer element and the probe-air interface. If the RTV lens material delaminates from the matching layer, an air pocket or bubble will occur between the two layers. This air pocket will be encountered by the transmitted pulse prior to reaching the probe-air interface, and an echo will be returned from this air pocket in advance of the reflection from the probe-air interface. If this is the problem the diagnostic processor will receive a waveform as shown in FIG. 7c. This waveform contains an echo 56 which precedes the expected echo signal at the one microsecond time point. Upon receipt of a waveform similar to that of FIG. 7c, the diagnostic processor will report a delamination of the layers of the probe lens.

Yet a further possibility is wearing or deformity of the RTV lens 34. Ultrasonic probes are often pressed hard or rubbed against the subject. This use can wear away or compress the lens material to a greater degree above one transducer element than others. This problem is detected by measuring the time of flight of the ultrasonic signal through the lens materials. A broadband transducer or system can be diagnosed for this problem by measuring the signal phase $\phi$ at a number of frequencies about the nominal center frequency of the transducer, then calculating the group delay for the element, the derivative of phase with respect to frequency, $d\phi/df$, a measure of the signal time of flight. The group delay of each transducer element is compared by the diagnostic processor with the group delays of the others to see if any are outside of predetermined tolerance limits. An out of tolerance group delay for a particular transducer element indicates a wearing or compression of the lens material above that element.

In a manner similar to that discussed for amplitude compensation, the beamformer operation can be adjusted by the diagnostic processor to compensate for time of flight variance. Time of flight variances can be caused by nonuniform thickness of the lens materials or by a problem with the transmission electronics. A time of flight inaccuracy can result in misregistration and defocusing of the signals combined in the beamformer output signal. If the received echo 50 or the measured group delay indicates an inaccuracy in time of reception of echoes, the beamformer delay for the channel can be adjusted to account for the variance and bring the signal of a particular channel back into focus with the signals processed by other channels of the beamformer.

Just as time of flight measurements detect performance variations in the time domain, the spectral characteristics of a received signal can be measured by the diagnostic processor to detect variations in the frequency domain. Variations in the bandwidth of the received signals and amplitude variations across the frequency band are measured by the diagnostic processor. The transfer function of an adaptive filter in the receive signal path can be varied in response to these measurements to compensate for such amplitude and frequency variations.

Even more sophisticated testing can be performed if there are two or more probes connected to the ultrasound system at the same time. When this is the case, the diagnostic processor is programmed to automatically test both probes and compare the waveforms received from both. The comparison is done among the elements of each probe as described above, and also from probe to probe. This enables the diagnostic processor 20 to isolate problems in the probe or in the channel electronics. For instance, if the test of element #15 on probe #1 yields a waveform as shown in FIG. 7a and a test of element #15 on probe #2 with the same channel electronics yields a waveform as shown in FIG. 6, the processor would conclude that the channel electronics is operating properly and that there is a problem with element #15 of probe #1. Alternatively if the two tests both yield a waveform such as that shown in FIG. 7b, the processor would conclude that there is a short in the receiver electronics.

It will be appreciated that different probes can have different lens thicknesses, and as a result the anticipated time of receipt of the echo from the probe-air interface can differ from one probe to another. This variation is accounted for by programming this characteristic in the probe's ID chip. Each probe carries a tiny read only memory in the probe connector that plugs into the ultrasound system. The read only memory is connected to several pins of the connector that mate with the system. When the connector is plugged into the system the system accesses and reads the contents of the read only memory. This information conventionally informs the systems of the type of probe (linear array, phased array, etc.), the probe serial number and the transducer bandwidth and center frequency. In accordance with the principles of the present invention, the read only memory is also programmed to contain information useful to the diagnostic processor such as lens thickness. If the probe is manufactured with a lens thickness that is not uniform across the transducer aperture, that information is also programmed into the read only memory. The expected group delay of the transducer elements is another piece of information that can be provided from the read only memory. This probe information is provided to the diagnostic processor and used by the processor in evaluating its test results.

There are a number of ways in which the diagnostic processor 20 can be controlled. The processor can be controlled from a set of controls or switches that are accessed by service personnel during periodic maintenance or inspection of the system. The service personnel are trained in the interpretation and analysis of the waveforms, and can best determine the nature and solution to any problems. The diagnostic processor 20 is connected to the system display 18 by way of the image and Doppler processor 16 and the processor can be commanded to display problems by means of text messages on the display or by the display of a fault revealing waveform stored by the processor. The display will provide the full context in which the waveform was detected, including the channel number, probe identification, transducer element number, and the time of the test. By reviewing this information the service person can quickly and easily identify problems and tend to their solution.

Another way to operate the diagnostic processor is to allow the user to command testing whenever the user feels that there may be a problem with the probe or system. A text message on the display informs the user of the results of the test at the conclusion of testing.

A third way to operate the diagnostic processor is to enable it to run automatically in the "background." The system controller or processor can detect when the system is sitting idle and not being used to diagnose patients. The passage of an extended period of time without the receipt of echo information is one such indicator of an idle condition. The diagnostic processor can be programmed under such condition to automatically test the channel electronics and connected probes during such periods of idleness. The testing can be full testing of all channels and transducer elements, or can be sample testing of only a selected number of channels and elements. The results of the test can be displayed on the display and viewed just before use of the system resumes, or can be stored in a test log and accessed when desired by the user or service personnel. The system would automatically cease testing and return to active patient scanning whenever a probe again comes into contact with a patient, which is immediately indicated by the presence of additional echo pulses between the probe-air interface echo 50 and its subsequent reflections 52, 54. It should be appreciated that such system-prompted automatic testing can provide inaccurate results if the probe has been left on the system with couplant gel still present on the lens. In consideration of such a possibility the diagnostic processor will generate a message to be read by the user or service person to check for such a condition and take it into consideration when assessing the results of system-prompted testing.

The diagnostic processor 20 can also be controlled to automatically begin testing the system and probes whenever it is first turned on. The user can be given the option if desired to either wait for the testing to be concluded before scanning patients, or to interrupt the testing and begin scanning a patient at once.

What is claimed is:

1. A method of testing the operability of an ultrasonic transducer probe or ultrasound system which has been manufactured and is suitable for operation by a user comprising the steps of:

connecting a multielement transducer probe to an ultrasound system;

activating the transducer probe by causing the transducer elements of the probe to transmit pulses with the acoustic window of the probe exposed to the air;

receiving echoes returned from the probe-air interface;

analyzing said received echoes returned from the probe-air interface with an analyzer integral to the ultrasound system to determine the operability of the transducer probe or ultrasound system.

2. The method of claim 1, wherein said ultrasound system contains a plurality of electronic channels connected to different transducer elements of the probe, and wherein the step of analyzing comprises the step of analyzing said received echoes to determine the operability of said transducer elements and their connections within the probe, or the operability of said electronic channels.

3. The method of claim 2, wherein said transducer elements are covered with an acoustic lens, and wherein the step of receiving comprises the step of receiving echoes returned from the lens-air interface.

4. An ultrasound system to which different multielement ultrasonic transducer probes may be connected for the performance of ultrasonic imaging or measurement, including means for testing the operability of a probe or the receive electronics of said system comprising:

means for connecting said ultrasound system to a multi-element transducer probe having an acoustic window overlaying said transducer elements;

means for causing the transducer elements of the probe to transmit pulses with the acoustic window of the probe not in contact with a patient;

channel electronics coupled for receiving echo signals returned from the exterior surface of said acoustic window; and a diagnostic processor, coupled to said channel electronics and integral to said ultrasound system, for analyzing said echo signals returned from the exterior surface of the acoustic window to determine the operability of the transducer probe or ultrasound system.

5. The ultrasound system of claim 4, wherein said diagnostic processor comprises means for analyzing the time of reception of said echo signals returned from the exterior surface of the acoustic window and the received waveform containing said echo signals to determine the integrity of an element of said transducer and its connections, or the integrity of the signal path of the channel electronics connected to said element.

6. The ultrasound system of claim 5, wherein said diagnostic processor includes means for determining the time of flight of signals received from a transducer element, and means for analyzing said time of flight to determine the integrity of said transducer probe.

7. The ultrasound system of claim 4, wherein said multielement transducer of said probe is covered with an acoustic lens, and wherein said diagnostic processor comprises means for analyzing said echo signals returned from the exterior surface of the acoustic lens to determine one of the conditions of a defective transducer element, and open circuit in series with said transducer element, a defective lens, and faulty electronics in the channel electronics coupled to said transducer element.

8. The ultrasound system of claim 4, further comprising control means, accessible to an operator of said ultrasound system, for commanding said diagnostic processor to conduct a test of said channel electronics and a multielement transducer probe.

9. The ultrasound system of claim 4, further comprising automatic control means coupled to said diagnostic processor for activating said processor to conduct testing of said channel electronics or a multielement transducer probe connected to said ultrasound system during periods when said system is not being used by a user to ultrasonically image or diagnose patients.

10. The ultrasound system of claim 4, further comprising means for computing the time of flight of signals received from a transducer element, and wherein said diagnostic processor includes means for utilizing said time of flight information to analyze the condition of said transducer probe.

11. The ultrasound system of claim 4, wherein said diagnostic processor further comprises means, responsive to the results of an analysis of said echo signals, for adjusting an operating characteristic of said channel electronics to improve the operability of said transducer probe or ultrasound system.

12. The ultrasound system of claim 11, wherein said adjusting means comprises means for adjusting the gain of said channel electronics.

13. The ultrasound system of claim 11, wherein said adjusting means comprises means for adjusting the time delay of said channel electronics.

14. The ultrasound system of claim 4, wherein said diagnostic processor includes means for measuring the amplitudes of signals received from a transducer element, and means for analyzing said measured amplitudes to determine the integrity of said transducer probe, transmit means or channel electronics.

15. The ultrasound system of claim 14, further comprising means, coupled to said channel electronics, for adjusting the signal gain of received echo signals to compensate for variations in signal amplitude.

16. The ultrasound system of claim 4, wherein said diagnostic processor includes means for measuring a characteristic of signals received from a transducer element as a function of frequency, and means for analyzing said measured frequency-dependent characteristic to determine the integrity of said transducer probe, transmit means or channel electronics.

17. The ultrasound system of claim 16, further comprising an adaptive filter, coupled to said channel electronics, for adjusting the filter transfer characteristic applied to received signals in response to a measured frequency-dependent characteristic.

* * * * *